United States Patent [19]

Diehl et al.

[11] Patent Number: 4,740,333

[45] Date of Patent: Apr. 26, 1988

[54] PROCESS FOR THE PREPARATION OF 5-FLUOROTOLUENE-2,4-DISULPHOCHLORIDE

[75] Inventors: Herbert Diehl, Leverkusen; Josef Käsbauer; Karlfried Wedemeyer, both of Cologne, all of Fed. Rep. of Germany

[73] Assignee: Bayer Aktiengesellschaft, Leverkusen, Fed. Rep. of Germany

[21] Appl. No.: 852,586

[22] Filed: Apr. 16, 1986

[30] Foreign Application Priority Data

May 3, 1985 [DE] Fed. Rep. of Germany ....... 3515870

[51] Int. Cl.[4] .......... C07C 143/70

[52] U.S. Cl. .......... 260/543 R; 260/505 R

[58] Field of Search .......... 260/543 R

[56] References Cited

PUBLICATIONS

Kirk-Othmer, *Encyclopedia of Chemical Technology*, 2nd., vol. 19, p. 282 and vol. 1, pp. 222–224.

Kirk-Othmer, *Encyclopedia of Chemical Technology*, Interscience, Publ. 2nd Ed., vol. 19, pp. 293–294, 301 and 313–314, 3rd Ed., vol. 22, pp. 7 and 45–48.

Journal of Pharmacy and Pharmacology, vol. 12, 1960, pp. 419–425, London, GB; B. G. Boggiano et al.: "Studies in the Field of Diuretic Drugs".

Journal of Organic Chemistry, vol. 27, Mar. 1962, pp. 951–956, Easton, U.S.: C. W. Whitehead et al.: "Diuretics. VI. 1,2,4–Benzothiadiazine 1,1–Dioxides Substituted at 2,3,4– and 7–N–Sulfamoyl Positions".

*Primary Examiner*—Michael L. Shippen

*Attorney, Agent, or Firm*—Sprung Horn Kramer & Woods

[57] ABSTRACT

5-Fluorotoluene-2,4-disulphochloride is prepared by chlorosulphonation of 3-fluorotoluene by first reacting the 3-fluorotoluene with chlorosulfuric acid and then with an inorganic acid chloride at temperatures up to 130° C. until the evolution of gas is complete, and then heating the reaction mixture at temperatures of up to 200° C. and, after the completion of the gas evolution, reacting the product at a lower temperature with further inorganic acid chloride, or reacting the 3-fluorotoluene with powerful sulphonating agents at an elevated temperature, if appropriate in the presence of inert solvents and/or diluents, to give the corresponding disulphonic acid and then treating the disulphonic acid with inorganic acid chlorides.

12 Claims, No Drawings

PROCESS FOR THE PREPARATION OF 5-FLUOROTOLUENE-2,4-DISULPHOCHLORIDE

BACKGROUND OF THE INVENTION

The invention relates to a process for the preparation of 5-fluorotoluene-2,4-disulphochloride by chlorosulphonation of 3-fluorotoluene.

It is known from *J. Pharm. Pharmacol.*, 12, 419 (1960) and *J. Org. Chem.*, 27, 951 (1962) to react 3-fluorotoluene with chlorosulphonic (chlorosulfuric) acid. Disadvantages in this process are the inadequate yields of approximately 50% of theory and the large excess of chlorosulphonic acid which is employed.

SUMMARY OF THE INVENTION

A process has now been found for the preparation of 5-fluorotoluene-2,4-disulphochloride by chlorosulphonation of 3-fluorotoluene, which process is characterized in that, first, the 3-fluorotoluene is reacted with chlorosulphonic acid and subsequently with an inorganic acid chloride at temperatures of up to 130° C. until the evolution of gas is complete, the reaction mixture is then heated at temperatures of up to 200° C. and, after the gas evolution is complete, the product is reacted at a lower temperature with further inorganic acid chloride, or the 3-fluorotoluene is reacted with powerful sulphonating agents at an elevated temperature, if appropriate in the presence of inert solvents and/or diluents, to give the corresponding disulphonic acid, and the disulphonic acid is subsequently reacted with inorganic acid chlorides.

DETAILED DESCRIPTION OF THE INVENTION

The following inorganic acid chlorides are suitable for the process according to the invention: thionyl chloride, phosphorus trichloride, phosphorus oxychloride, phosphorus pentachloride and/or phosgene, preferably thionyl chloride.

The following may be mentioned as powerful sulphonating agents: oleum, $SO_3$, $SO_3$ adducts, such as pyridine-$SO_3$, and/or sulphuric acid, preferably $SO_3$ (sulfur trioxide).

The reaction according to the invention of 3-fluorotoluene with chlorosulphonic acid and subsequently with an inorganic acid chloride is advantageously carried out at temperatures from 70° to 130° C., preferably at temperatures from 90° to 100° C. In the main, the corresponding monosulphochloride is formed in this reaction. When the gas evolution is complete, it is advantageous to heat the reaction mixture at temperatures from 130° to 200° C., preferably at temperatures from 150° to 170° C. When the gas evolution is complete, the reaction mixture is cooled, generally to temperatures of about 50° to 130° C., preferably 70° to 100° C., and is reacted with further inorganic acid chloride (variant 1).

In accordance with another process variant (variant 2) the 3-fluorotoluene is first reacted with powerful sulphonating agents at temperatures within the range from about 50° to 120° C., preferably 90° to 110° C., if appropriate in the presence of inert solvents and/or diluents, to give the disulphonic acid, and is subsequently reacted with inorganic acid chlorides to give the corresponding disulphochloride.

The following, above all, are suitable as inert solvents and/or diluents in this reaction: sulphuric acid and chlorosulphonic acid, preferably chlorosulphonic acid.

The inert solvents and/or diluents can be employed either on their own or as a mixture with one another. The amount of the solvents and/or diluents employed is not critical and can vary within wide ranges. Usually, an amount of about 20 to 200, preferably 30 to 100, % by weight, relative to 3-fluorotoluene, is employed.

In the reaction according to the invention, the chlorosulphonic acid is generally employed in an amount of about 2 to 5 moles, preferably 2 to 2.5 moles, per mole of 3-fluorotoluene.

The amount of inorganic acid chloride is usually approximately 2 to 4 moles, preferably 2 to 3 moles, per mole of 3-fluorotoluene. In this respect, in variant 1 the reaction is first carried out with 0.5 to 2 moles, preferably 1 to 1.5 moles, of inorganic acid chloride per mole of 3-fluorotoluene, and, after the completion of the gas evolution, the reaction mixture is then reacted with further inorganic acid chloride (approximately 0.5 to 2 moles, preferably 1 to 1.5 moles, per mole of 3-fluorotoluene).

The amount of strong sulphonating agent employed in accordance with the invention is generally about 2 to 4 moles, preferably 2 to 2.5 moles, per mole of 3-fluorotoluene.

After the completion of the reaction according to the invention, the 5-fluorotoluene-2,4-disulphochloride can be isolated by distilling off excess thionyl chloride and chlorosulphonic acid. A further possible means of isolating the reaction product is to pour the reaction mixture into ice water and to filter off the precipitated product with suction. The crude product can be purified by being distilled or recrystallized from a suitable solvent, for example ligroin.

However, in accordance with the process according to the invention the 5-fluorotoluene-2,4-disulphochloride is obtained in such a high state of purity that it can be processed further directly without further purification.

The advantage of the process according to the invention compared with the state of the art is that pure (up to 99.8%), isomer-free 5-fluorotoluene-2,4-disulphochloride is obtained in a yield of up to approximately 98%, and, as a result of the small excess of sulphonating agent, no unnecessary exit air and effluent problem arises through working up excess sulphonating agents by hydrolysis, and/or the removal by distillation of large amounts of sulphonating agent, which is an expensive technical operation, is avoided.

The 5-fluorotoluene-2,4-disulphochloride obtained can be chlorinated in a known manner to give 2,4-dichloro-5-fluorobenzotrichloride (see German Patent Specification 234,913; Frdl. 10, 117), and can be reacted further, by partial hydrolysis catalysed by $FeCl_3$, to give 2,4-dichloro-5-fluorobenzoyl chloride (see *Ullmanns Encyclopädie der technischen Chemie* ["Ullmann's Encyclopaedia of Industrial Chemistry"], volume 8, page 373, 4th edition, 1974).

2,4-Dichloro-5-fluorobenzoyl chloride is a valuable intermediate product for the preparation of antibacterial medicaments, in particular 1-cyclopropyl-6-fluoro-1,4-dihydro-7-(1-piperazinyl)-4-oxoquinolinecarboxylic acid of the formula shown below (see DE-OS (German Published Specification) 3,033,157):

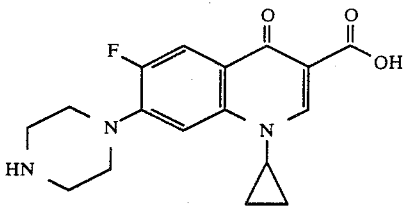

EXAMPLES

Example 1

396 g (3.60 moles) of 3-fluorotoluene are added dropwise, in the course of 65 minutes, to 876 g (7.25 moles, 0.7% excess) of chlorosulphonic acid (96–97% strength). The mixture is stirred for one hour at 97°–99° C. and is allowed to cool to 89° C. and 588 g (4.94 moles) of thionyl chloride are added dropwise in the course of 75 minutes. Stirring is continued at 90°–95° C. for 30 minutes and the mixture is heated up to 160° C. in the course of 75 minutes. When the gas evolution is complete, 402 g (3.38 moles) of thionyl chloride are added dropwise at 78° C. in the course of one hour. The mixture is stirred at 120° C. until the gas evolution is complete. Excess thionyl chloride and a little chlorosulphonic acid are removed by distillation. The product crystallizes out on cooling. Yield 1,087 g, 98.3% of theory, purity 99.8%.

Example 2

99 g (0.899 mole) of 3-fluorotoluene are added dropwise, at 50°–80° C. and in the course of 60 minutes, to 146 g (1.824 moles) of $SO_3$. Stirring is continued for one hour at 106° C., 25 ml of chlorosulphonic acid are added and 248 g (2.084 moles) of thionyl chloride are added dropwise at 80°–90° C. The mixture is stirred at 120° C. until gas evolution is complete. Working up is carried out as in Example 1. Yield 268.5 g, 97.2% of theory, purity 98.7%.

It will be appreciated that the instant specification and claims are set forth by way of illustration and not limitation, and that various modifications and changes may be made without departing from the spirit and scope of the present invention.

We claim:

1. A process for the preparation of 5-fluorotoluene-2,4-disulphochloride by chlorosulphonation of a 3-fluorotoluene, comprising (i)(a) reacting the 3-fluorotoluene with chlorosulfonic acid and then with an acid chloride, said acid chloride being thionyl chloride, at temperatures of 70° C. to 130° C. until the evolution of gas is complete, said chlorosulfuric acid being employed in the amount of 2 to 5 moles per mole of said 3-fluorotoluene, (i)(b) heating the resultant reaction mixture from step (i)(a) at a temperature of 130° C. to 200° C. and, after the gas evolution is complete, (i)(c) reacting the product of step (i)(b) at a lower temperature with further of said acid chloride, or, (ii) reacting the 3-fluorotoluene with a sulphonating agent selected from the group consisting of oleum, sulphur trioxide, sulphur trioxide adducts, sulphuric acid and mixtures thereof at an elevated temperature to yield a corresponding disulphonic acid, wherein 2 to 4 moles of said sulphonating agent are employed per mole of said 3-fluorotoluene, and reacting the disulphonic acid with said acid chloride, wherein for the entire process (i) or (ii) 2 to 4 moles of said acid chloride are employed per mole of 3-fluorotoluene.

2. A process according to claim 1, wherein the 3-fluorotoluene in step (i)(a) is reacted at a temperature from 90° C. to 100° C. with said chlorosulfuric acid and subsequently with said acid chloride.

3. A process according to claim 1, wherein the resultant reaction mixture from step (i)(b) is heated at a temperature of 150° C. to 170° C.

4. A process according to claim 1 wherein the chlorosulfuric acid is employed in an amount of 2 to 2.5 moles per mole of 3-fluorotoluene.

5. A process according to claim 1, wherein for the entire process 2 to 3 moles of said acid chloride are employed per mole of 3-fluorotoluene.

6. A process according to claim 1, wherein said sulphonating agent is sulfur trioxide.

7. A process according to claim 1, wherein the reacting of said 3-fluorotoluene with said sulphonating agent in (ii) is conducted in the presence of solvents and/or diluents.

8. A process according to claim 7, wherein the inert solvents and/or diluents are employed in an amount of about 20 to 200% by weight relative to said 3-fluorotoluene.

9. A process according to claim 7, wherein the solvents and/or diluents are selected from the group consisting of sulphuric acid and chlorosulfuric acid.

10. A process according to claim 1, wherein in (ii) the reacting of the 3-fluorotoluene and the sulphonating agent is conducted at a temperature of 50° C. to 120° C.

11. A process according to claim 1, wherein said temperature in step (i)(b) is 50° C. to 130° C.

12. A process according to claim 1, wherein for step (i)(a) the moles of acid chloride per mole of 3-fluorotoluene is 0.5 to 2 moles and for step (i)(c) the moles of acid chloride per moles of 3-fluorotoluene is is 0.5 to 2 moles.

* * * * *

UNITED STATES PATENT AND TRADEMARK OFFICE

CERTIFICATE OF CORRECTION

PATENT NO. : 4,740,333

DATED : April 26, 1988

INVENTOR(S) : Herbert Diehl, et al.

It is certified that error appears in the above-identified patent and that said Letters Patent is hereby corrected as shown below:

Col. 3, line 51 — Delete "chlorosulfonic" and substitute --chlorosulfuric--

Signed and Sealed this

First Day of November, 1988

*Attest:*

DONALD J. QUIGG

*Attesting Officer* — *Commissioner of Patents and Trademarks*